(12) United States Patent
Bogdanovich

(10) Patent No.: US 10,413,623 B2
(45) Date of Patent: Sep. 17, 2019

(54) PORTABLE GERMICIDAL PANEL

(71) Applicant: Phillip Bogdanovich, Austin, TX (US)

(72) Inventor: Phillip Bogdanovich, Austin, TX (US)

( * ) Notice: Subject to any disclaimer, the term of this patent is extended or adjusted under 35 U.S.C. 154(b) by 0 days.

(21) Appl. No.: 15/612,692

(22) Filed: Jun. 2, 2017

(65) Prior Publication Data

US 2017/0348445 A1   Dec. 7, 2017

Related U.S. Application Data

(60) Provisional application No. 62/345,510, filed on Jun. 3, 2016.

(51) Int. Cl.

| | |
|---|---|
| *A61L 2/08* | (2006.01) |
| *F21V 23/06* | (2006.01) |
| *A61L 2/10* | (2006.01) |
| *F21V 5/00* | (2018.01) |
| *F21V 23/00* | (2015.01) |
| *F21Y 115/10* | (2016.01) |

(Continued)

(52) U.S. Cl.
CPC ............. *A61L 2/10* (2013.01); *A61L 2/084* (2013.01); *A61L 2/085* (2013.01); *F21V 5/007* (2013.01); *F21V 23/003* (2013.01); *F21V 23/06* (2013.01); *A61L 2202/12* (2013.01); *A61L 2202/123* (2013.01); *A61L 2202/24* (2013.01); *F21K 9/238* (2016.08); *F21K 9/278* (2016.08); *F21Y 2115/10* (2016.08)

(58) Field of Classification Search
None
See application file for complete search history.

(56) References Cited

U.S. PATENT DOCUMENTS

| | | | |
|---|---|---|---|
| 7,080,927 B2 * | 7/2006 | Feuerborn | F21S 2/005 362/238 |
| 2005/0007780 A1 * | 1/2005 | Feuerborn | F21S 2/005 362/257 |

(Continued)

FOREIGN PATENT DOCUMENTS

| | | | | | |
|---|---|---|---|---|---|
| KR | 20100024073 A | * | 3/2010 | ............ | F21V 21/002 |
| KR | 20110007994 U | * | 8/2011 | ................ | F21S 4/00 |
| KR | 20130050453 A | * | 5/2013 | ................ | F21S 2/00 |

OTHER PUBLICATIONS

Translated DERWENT abstract of KR20110007994U (Year: 2011).*
Machine Translation of KR20110007994U from EPO (Year: 2011).*
Machine Translation of KR20100024073 from EPO (Year: 2010).*

*Primary Examiner* — Michael J Logie
(74) *Attorney, Agent, or Firm* — Akerman LLP; Mammen P. Zachariah, Jr.

(57) ABSTRACT

A germicidal device is disclosed. The germicidal device may include a flexible panel that can be rolled up and/or folded. A plurality of LEDs embedded in the panel and a plurality of lenses are embedded in the panel. The panel includes an input connector coupled to the panel that receives input at a first voltage from a power source. The LEDs are coupled to the input connector and provided a second voltage that is suitable for operating the LEDs. The panel also includes one or more output connectors on the panel. The output connectors provide the first voltage as an output voltage from the panel. The panel may be coupled to additional panels with the additional panels receiving the first (output) voltage from the first panel as input voltage to the additional panels.

20 Claims, 2 Drawing Sheets

(51) Int. Cl.
*F21K 9/238* (2016.01)
*F21K 9/278* (2016.01)

(56) References Cited

U.S. PATENT DOCUMENTS

| | | | |
|---|---|---|---|
| 2011/0141736 A1* | 6/2011 | Lin | F21S 2/005 |
| | | | 362/240 |
| 2011/0243789 A1* | 10/2011 | Roberts | A61L 2/10 |
| | | | 422/24 |
| 2016/0281941 A1* | 9/2016 | Cousin | E04B 9/0478 |
| 2017/0246331 A1* | 8/2017 | Lloyd | A61L 2/084 |
| 2017/0254518 A1* | 9/2017 | Vasylyev | F21V 21/14 |

* cited by examiner

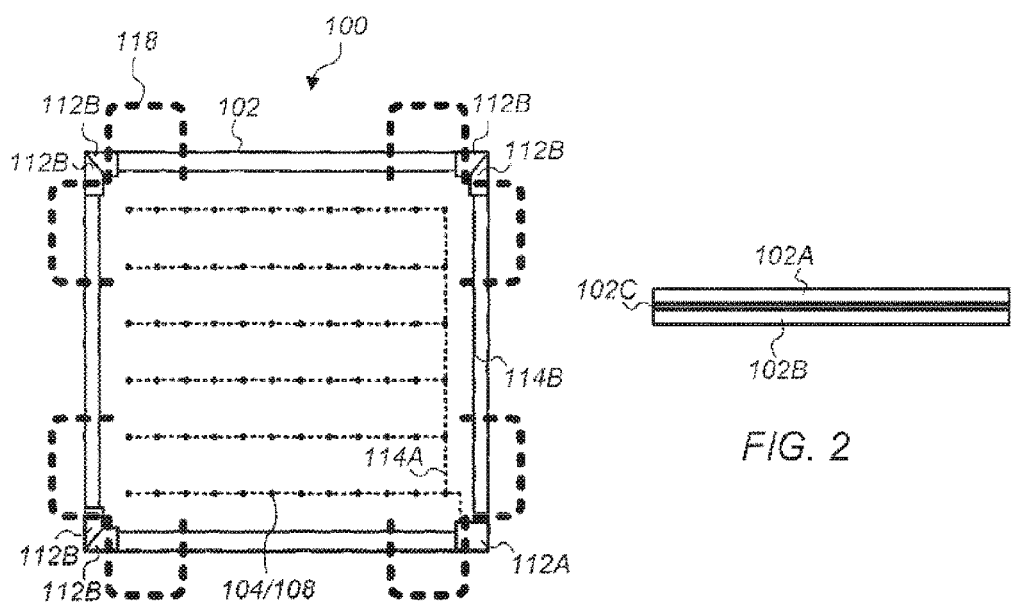
FIG. 1
FIG. 2
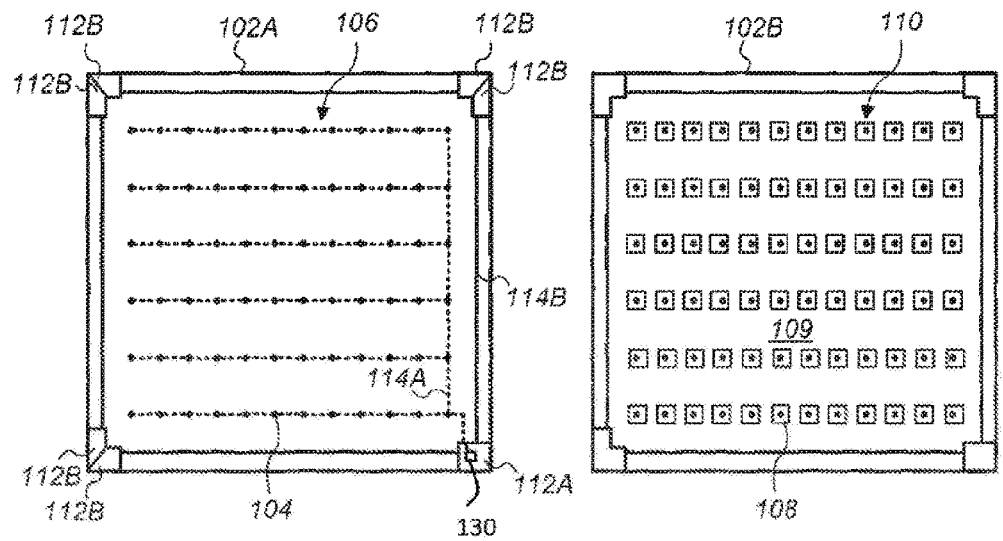
FIG. 3

PORTABLE GERMICIDAL PANEL

PRIORITY CLAIM

This patent claims priority to U.S. Provisional Patent Application No. 62/345,510 to Bogdanovich, entitled "PORTABLE GERMICIDAL MAT", filed Jun. 3, 2016, which is incorporated by reference in its entirety.

BACKGROUND OF THE INVENTION

1. Field of the Invention

Embodiments disclosed herein relate to the use of a panel(s) for germicidal sterilization. Certain embodiments disclosed herein relate to a portable mat with LEDs (light-emitting diodes) for germicidal sterilization.

2. Description of the Relevant Art

Medical equipment and spaces are continually in need of sterilization to remove germs and create a clean and safe environment for patient treatment. Current sterilization methods often include the use of chemical cleansing methods. For example, bleach, Hibiclens®, iodine, and/or isopropyl alcohol are often used to chemically clean medical equipment and medical spaces. Chemical solutions, however, can be messy and difficult to work with in addition to being environmentally unfriendly. Human tissue may also be damaged by some chemical solutions.

In 1877, Dr. Arthur Downes and Dr. Thomas Blunt made the discovery that sunlight, which includes ultraviolet (UV) light, has a germicidal effect on bacteria. Continuous research since that discovery has shown that specifically UVB and UVC light are capable of destroying 99% of bacteria and viruses. UV lights have been used as a method of decontamination (sterilization) in limited applications since the 1950s. In the 1990s, near-UV and blue light exposure was found to sufficiently damage the surface of numerous types of bacteria to render the bacteria inactive.

In 2005, ongoing research at Strathclyde University showed that near-UV LED (light-emitting diode) light exposure at 405 nm was sufficient to produce similar results to previous UV light research. UVC and UVB light, however, may cause damage to human tissue and cannot be used (under most conditions) directly on human tissue. Blue and near-UV LEDs may also be fragile and difficult to deploy, especially at portable or remote medical spaces.

Heat may also be used to sterilize surfaces. For example, heating the surface or the surrounding air around the surface may sufficiently heat microbials (bacteria) until they die. The temperatures required to destroy most types of bacteria, however, are temperatures at which human tissue (or other organic material) is damaged or decomposes. In some cases, heat may be used in combination with chemical solutions (such as those described above).

Strathclyde University developed a UV ceiling module that utilizes LED diodes comingled with other types of LEDs. The comingling provides scotopic values of near-UV (violet) with actual photopic values being significantly higher. The mixing of the light does not produce a functional average wavelength (e.g., 200 nm+400 nm=600 nm, etc.) but rather a mix of wavelengths (e.g., 200 nm comingled with 600 nm). Germicidal efficiency may be determined by the intensity (lux) and spectral wavelength (nm). Because intensity is a product of the number of devices producing a specific wavelength of light, the comingling produced fewer lux than necessary at the appropriate wavelength in the UV ceiling module. The low germicidal efficacy, in addition to other problems, kept the UV ceiling module from being an accepted product.

Ionizing lamps (e.g., UV ionizing lamps) have also been used to provide germicidal sterilization. These lamps, however, often use low voltage current (e.g., household 120 V current) that passes through exposed wires to "ionize" the immediate environment. The wavelength of the UV lights integrated into these devices is inappropriate to provide any germicidal effect. These lights are typically considered as more gimmick than functional for germicidal sterilization.

UVC LED deployments are another design that has been used to attempt germicidal sterilization. UVC light, as discussed above, however, may adversely affect human tissue exposed to the UVC light. For example, direct contact with UVC light for prolonged periods may cause burns and/or cellular changes consistent with certain types of cancer. UVC does, however, have high germicidal sterilization efficacy so is a usable solution for sterilization when no direct human contact is needed (e.g., uses other than physical evaluation or treatment of a patient). Thus, there remains a need for a germicidal device that is non-chemical, non-toxic, effective, easily deployable (e.g., portable), and safe for use in a variety of medical spaces. Such a device may be especially useful for temporary medical facilities used in military engagements, natural disaster scenarios, or other short term medical deployment situations.

SUMMARY OF THE INVENTION

In certain embodiments, a germicidal device includes: a panel; a plurality of LEDs embedded in the panel; a plurality of lenses embedded in the panel, wherein at least one lens is aligned with at least one LED; at least one input connector located on the panel, wherein the at least one input connector is configured to receive an input voltage from a power source; a first wiring located on the panel, the first wiring being coupled to the at least one input connector and to one or more of the LEDs; a driver circuit coupled to the first wiring, wherein the driver circuit receives the input voltage and provides a drive voltage to the one or more LEDs through the first wiring; a second wiring located on the panel, the second wiring being coupled to the at least one input connector; and at least one output connector coupled to the second wiring, wherein the at least one output connector receives the input voltage from the at least one input connector through the second wiring, and wherein the at least one output connector provides an output voltage that is substantially identical to the input voltage received from the power source.

In some embodiments, the panel is made of flexible material and may be rolled up and/or folded into a compact shape for portability. The panel may include two panel portions, the plurality of LEDs being embedded in a first panel portion and the plurality of lenses being embedded in the second panel portion. The panel portions may be coupled together with an additional material to form the panel.

In some embodiments, the LEDs are configured to provide germicidal illumination when turned on. The LEDs may include LEDs with a wavelength between about 405 nm and about 450 nm. The output voltage provided by the output connectors may include the input voltage without modification. The panel may be configured to be connected to at least one additional panel. The additional panel may include at least one input connector coupled to at least one output connector of the panel.

In certain embodiments, a germicidal device system includes: two or more panels, each panel including: a plurality of LEDs embedded in the panel, wherein the LEDs are positioned in the panel; a plurality of lenses embedded in the panel, wherein at least one lens is aligned with at least one LED; at least one input connector located on the panel, wherein the at least one input connector is configured to receive a first voltage; a first wiring located on the panel, the first wiring being coupled to the at least one input connector and to one or more of the LEDs; a driver circuit coupled to the first wiring, wherein the driver circuit receives the first voltage and provides a second voltage to the one or more LEDs through the first wiring; a second wiring located on the panel, the second wiring being coupled to the at least one input connector; and at least one output connector coupled to the second wiring, wherein the at least one output connector receives the first voltage from the at least one input connector through the second wiring, and wherein the at least one output connector outputs the first voltage. A first panel may be configured to be coupled to a second panel by coupling the at least one output connector on the first panel to the at least one input connector on the second panel, wherein the first panel receives the first voltage from a power source through the at least one input connector on the first panel and provides the first voltage to the second panel, the second panel receiving the first voltage through the at least one input connector on the second panel.

BRIEF DESCRIPTION OF THE DRAWINGS

Features and advantages of the methods and apparatus described herein will be more fully appreciated by reference to the following detailed description of presently preferred but nonetheless illustrative embodiments when taken in conjunction with the accompanying drawings in which:

FIG. 1 depicts a representation of an embodiment of a germicidal device.

FIG. 2 depicts a side-view representation of an embodiment of a panel.

FIG. 3 depicts top-view representations of a first panel portion and a second panel portion.

Figure 4:
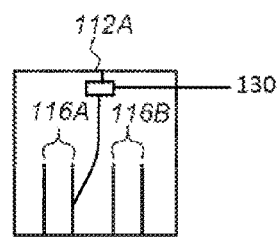
FIG. 4 depicts an enlarged representation of a power connector.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form illustrated, but on the contrary, the intention is to cover all modifications, equivalents and alternatives falling within the spirit and scope of the present disclosure as defined by the appended claims. The headings used herein are for organizational purposes only and are not meant to be used to limit the scope of the description. As used throughout this application, the word "may" is used in a permissive sense (i.e., meaning having the potential to), rather than the mandatory sense (i.e., meaning must). Similarly, the words "include," "including," and "includes" mean including, but not limited to. Additionally, as used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Various units, circuits, or other components may be described as "configured to" perform a task or tasks. In such contexts, "configured to" is a broad recitation of structure generally meaning "having structure that" performs the task or tasks during operation. As such, the unit/circuit/component can be configured to perform the task even when the unit/circuit/component is not currently on. Similarly, various units/circuits/components may be described as performing a task or tasks, for convenience in the description. Such descriptions should be interpreted as including the phrase "configured to." Reciting a unit/circuit/component that is configured to perform one or more tasks is expressly intended not to invoke 35 U.S.C. § 112(f) interpretation for that unit/circuit/component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF EMBODIMENTS

The following examples are included to demonstrate preferred embodiments. It should be appreciated by those of skill in the art that the techniques disclosed in the examples which follow represent techniques discovered by the inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

This specification includes references to "one embodiment" or "an embodiment." The appearances of the phrases "in one embodiment" or "in an embodiment" do not necessarily refer to the same embodiment, although embodiments that include any combination of the features are generally contemplated, unless expressly disclaimed herein. Particular features, structures, or characteristics may be combined in any suitable manner consistent with this disclosure.

FIG. 1 depicts a representation of an embodiment of germicidal device 100. Device 100 may include one or panels 102. For simplicity in the drawing, device 100 is shown with one panel 102 in FIG. 1. Panel 102 may be a rubber panel or a panel made of another lightweight, flexible material. In some embodiments, panel 102 is a mat or similar. In one embodiment, panel 102 is made of a thermoplastic elastomer material. In certain embodiments, panel 102 is made a material that allows the panel to be rolled up and/or folded into a more compact shape (e.g., similar to a yoga mat or a placemat). Panel 102 may be made of a material that is non-toxic, inert, and safe for use in a variety of medical spaces. Rolling up and/or folding panel 102 allows the panel to be more easily stored and/or moved (e.g., moved between different deployments of device 100).

In certain embodiments, panel 102 is a square shaped panel. For example, panel 102 may be a 3'×3' panel. Panel 102 may have other sizes and/or other shapes (e.g., a rectangle) depending on an intended use of the panel. For example, a smaller panel may be used to provide the panel with more portability (e.g., so the panel can be placed in a backpack or rucksack).

FIG. 2 depicts a side-view representation of an embodiment of panel 102. In certain embodiments, panel 102 includes two panel portions 102A, 102B. Panel portions 102A, 102B may be coupled together (e.g., attached or bonded to each other) to form panel 102. For example, panel portions 102A, 102B may be coupled together using foam tape or another flexible adhesive material. In some embodiments, additional flexible material 102C (e.g., flexible rubber) is placed between panel portions 102A, 102B. Flexible material 102C may provide additional flexibility to panel 102.

FIG. 3 depicts top-view representations of panel portion 102A and panel portion 102B. In certain embodiments, panel portion 102A and panel portion 102B include different integrated components. For example, in one embodiment, panel portion 102A includes LEDs 104 (light emitting diodes 104) embedded or integrated into the panel portion. LEDs 104 may be positioned in array 106 in panel portion 102A. Panel portion 102A may be a flexible material to allow the panel portion (and panel 102) to be rolled up and/or folded without damaging LEDs 104.

Panel portion 102B may include lenses 108 embedded or integrated into the panel portion. Lenses 108 may be positioned in array 110 in panel portion 102B. Lenses 108 may be any lens suitable to transmit light from LEDs 104 and protect the LEDs from the environment. In certain embodiments, space 109 between lenses 108 in panel portion 102B (e.g., the negative space between lenses) includes flexible material (e.g., flexible or non-rigid membrane material). In some embodiments, space 109 in panel portion 102B includes material that is molded around lenses 108. For example, lenses 108 may be positioned in a mold. The mold may then be filled with a material that surrounds lenses 108 (e.g., fills space 109) and cures or solidifies into the flexible material in the space between lenses to form panel portion 102B. Thus, panel portion 102B is formed with lenses 108 in array 110 and space 109 being flexible material between the lenses. Using the mold to form panel portion 102B may allow a single mold to be designed and used to produce multiple panel portions having array 110 and space 109 between lenses 108. Using flexible material in space 109 in panel portion 102B allows the panel portion (and panel 102) to be rolled up and/or folded without damaging lenses 108. Thus, panel portion 102B may be combined with panel portion 102A to form panel 102 that may be rolled up and/or folded without damaging LEDs 104 and/or lenses 108.

In certain embodiments, when panel portion 102A is coupled to panel portion 102B, LEDs 104 and lenses 108 are aligned so that each LED on panel portion 102A is aligned with a corresponding lens 108 on panel portion 102B. For example, array 106 and array 110 may be similarly arranged arrays that align when the panel portions are coupled to form panel 102. Thus, when panel portion 102A and panel portion 102B are coupled together to form panel 102, as shown in FIGS. 1 and 2, lenses 108 are aligned with and cover LEDs 104 to provide a secure, protected environment for the LEDs.

In certain embodiments, lenses 108 in array 110 have individually selectable optical properties. For example, each lens 108 in array 110 may have its own selected optical properties. Examples of optical properties that may be selected for each lens 108 in array 110 include, but are not limited to, beam angle (or beam angle between lenses), index of refraction, transmission efficiency, focus, magnification, and diffusion. Since each lens 108 is aligned with a corresponding LED 104 in array 106, having individually selectable optical properties for lenses 108 in array 110 allows each lens to provide individually desired properties for its corresponding LED. For example, in some embodiments, it may be desirable to have the beam angle for LEDs to vary from the edge of panel 102 to the center of the panel to provide desired light output. Thus, having individually selectable optical properties for lenses 108 in array 110 allows panel 102 to be designed for specific applications by selecting different lens properties for each lens in the array as needed.

As shown in FIG. 1, panel 102 may include one or more power connectors 112 on the panel. In certain embodiments, one or more power connectors 112 are located at each corner of panel 102. Power connectors 112 may be, for example, power plugs or other power connectors with multiple pins in the connector. Power connectors 112 may be connectors suitable for coupling to various power sources. For example, power connectors 112 may be suitable for coupling to a 120V AC power source, a 277V AC power source, and/or a 12V DC power source.

In certain embodiments, power connector 112A is located at one corner of panel 102 while power connectors 112B are located at the other corners of the panel. For example, in one embodiment, as shown in FIG. 1, power connector 112A is at the lower right corner of panel 102 while other corners of the panel have at least two power connectors 112B at each corner. Power connector 112A may provide a power input connector for panel 102 while power connectors 112B provide power output connectors for the panel as described below. In certain embodiments, power connector 112A is a male power connector while power connectors 112B are female power connectors. In some embodiments, power connector 112A is adapted to be coupled to power connectors 112B (e.g., the power connectors are a male-female pair of connectors). In some embodiments, power connector 112A is adapted to be coupled to another connector (not shown) to provide connection to a particular power source (e.g., another connector may be used to adapt power connector 112A for connecting to an AC or DC power source).

FIG. 4 depicts an enlarged representation of power connector 112A. Power connector 112A may include a plurality of pins 116. In certain embodiments, power connector 112A includes two sets of pins-pins 116A and pins 116B. As shown in FIG. 1, pins 116A may provide connection to wiring 114A in panel 102 while pins 116B may provide connection to wiring 114B in the panel. Wiring 114A may be a driver circuit and provide connection between power connector 112A and LEDs 104 on the interior of panel 102. In certain embodiments, pins 116A transform voltage input on the pins to a suitable voltage for driving LEDs 104. For example, pins 116A may step down and/or transform any desired input voltage (e.g., 120V AC, 12V DC, etc.) to a DC voltage suitable for driving (powering) LEDs 104. In some embodiments, a transformer or driver circuit 130 is coupled to pins 116A and wiring 114A to transform the voltage input on the pins to a suitable voltage for driving LEDs 104.

Wiring 114B may be a closed power circuit (e.g., a racetrack circuit) that provides a power connection between power connector 112A and power connectors 112B along the edge of panel 102. Wiring 114B may be conductive wiring such as copper or silver. In certain embodiments, wiring 114B provides power between power connector 112A and power connectors 112B without modifying the voltage of the power input to panel 102 through power connector 112A. Thus, the input voltage at power connector 112A is provided as an output voltage at power connectors 112B (e.g., the input voltage is passed through from power connector 112A to power connectors 112B through wiring 114B).

Providing the unmodified output voltage at each of power connectors 112B using wiring 114B allows one or more additional panels (e.g., panels substantially identical to panel 102) to be connected to panel 102 and receive power from panel 102. For example, power connector 112A on an additional panel connects to one of power connectors 112B on panel 102 to receive power from panel 102. The additional panels may operate at the same voltage as panel 102 with a single power source providing power to all the panels connected together (e.g., all the panels use a single power source connected to panel 102). Thus, providing unmodified output voltage at power connectors 112B allows multiple panels to be attached to panel 102 with all the panels electrically coupled together. For example, multiple panels 102 may be attached together in a modular pattern (e.g., a tile pattern) because the panels are modular (e.g., substantially identical with corresponding input/output connectors).

Figure 5:
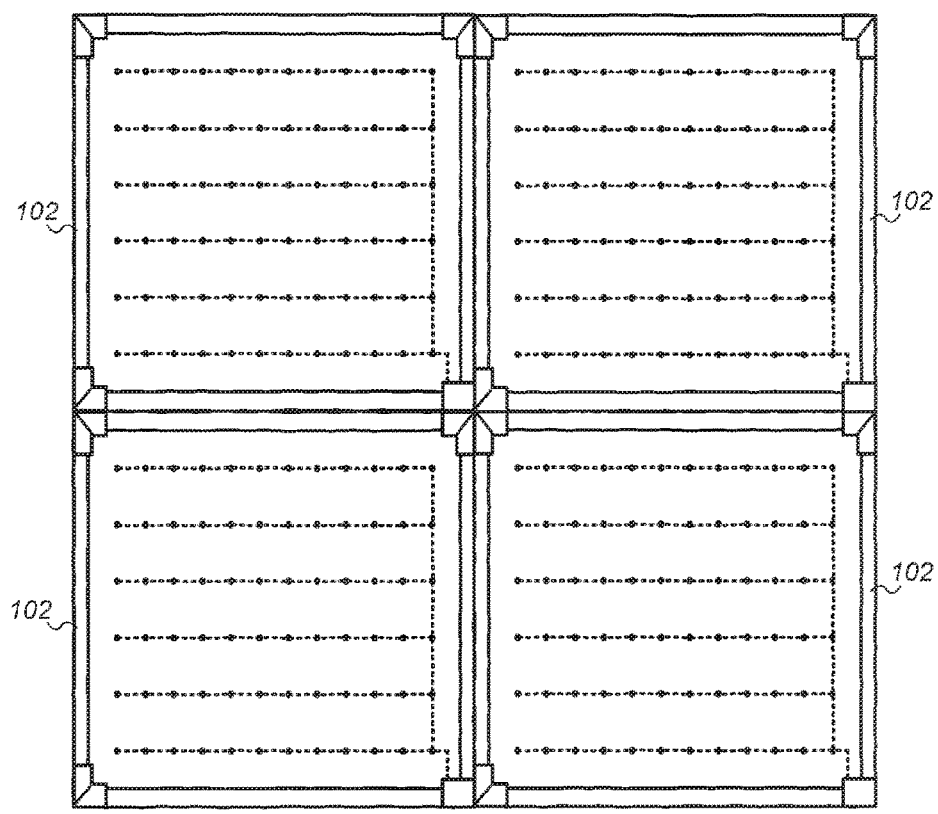
FIG. 5 depicts a representation of an embodiment of a germicidal device with four panels attached and electrically coupled together.

FIG. 5 depicts a representation of an embodiment of germicidal device 100 with four panels 102 attached and electrically coupled together. Attaching and powering multiple panels together allows a larger germicidal device to be created as needed by attaching a desired number of panels together and powering the panels with the single power source. The number of panels may be adjusted as needed as long as sufficient power is available for each of the panels being connected to form the larger germicidal device (e.g., the panel most distant from the power source has sufficient power to drive LEDs 104 on the panel). Adjusting the number of panels 102 in germicidal device 100 may increase intensity and/or effective coverage area of the germicidal device.

In certain embodiments, LEDs 104 are LEDs that have selected germicidal properties. For example, LEDs 104 may be LEDs that provide a minimum germicidal (bactericidal) efficiency. In certain embodiments, LEDs 104 are LEDs with a wavelength in a range of about 405 nm to about 450 nm. LEDs 104 with such wavelengths may provide a germicidal efficiency of 95% or more. With such germicidal efficiency, panel 102 may create a medically clean environment in about 5 minutes in a space illuminated by LEDs 104 (e.g., a space in front of the panel). Other wavelength ranges may also be contemplated for LEDs 104. For example, in some embodiments, LEDs 104 are LEDs with a wavelength in a range between about 10 nm and about 100 μm. In some embodiments, LEDs 104 are LEDs with a wavelength in a range between about 100 nm and about 10 μm. In some embodiments, LEDs 104 are LEDs with a wavelength in a range between about 100 nm and about 1 μm.

In some embodiments, LEDs 104 include LEDs with additional wavelengths and/or combinations of different wavelength LEDs. For example, LEDs 104 may include near-UV LEDs, extreme-UV LEDs, UVC LEDs, UVB LEDs, UVA LEDs, LEDs in the visible light spectrum (e.g., RGB LEDs with wavelengths in a range between about 450 nm and about 750 nm), IR LEDs, far IR LEDs, or combinations of one or more of these LEDs. Regardless of the type(s) of LEDs used in LEDs 104, at least some light amount of UV and/or near-UV light may be needed to provide germicidal efficacy using LEDs 104. Thus, the germicidal efficacy of LEDs 104 may be dependent upon the amount of UV, near-UV, or UV+near-UV light (amount may be measured, for example, in foot candles) emitted onto a surface irrespective of any other light being provided. For instance, if an RGB LED is producing 15 foot candles of light on a surface and a 415 nm near-UV LED is producing 5 foot candles on the same surface at the same time, the germicidal efficacy is related to the output of the near-UV LED. While both LEDs are emitting some light on the surface, only the near-UV LED (or any UV/UV+near-UV LEDs) is providing any germicidal effect on the surface.

In some embodiments, however, it may be useful to provide alternative light in addition to UV, near-UV, or UV+near-UV light. For example, use of RGB LEDs may provide some amount of colored light on a surface (e.g., some light will have visible wavelengths) while the UV, near-UV, or UV+near-UV LEDs provide at least some light with wavelengths suitable to provide a germicidal effect on the surface. The combination of the RGB LEDs and the UV, near-UV, or UV+near-UV LEDs may create a visible color (wavelength) effect not rendered on the surface by either of the different LEDs on their own. Providing the visible color effect due to the combination of LEDs may provide an indication to a user that both sets of LEDs are working and that the germicidal effect of panel 102 is active on the surface.

In certain embodiments, as shown in FIG. 1, panel 102 includes at least one switch 118. Switch 118 may be coupled to wiring 114A and provide control for turning on/off LEDs 104. For example, switch 118 may be a toggle or pushbutton switch inline with wiring 114A to turn on/off LEDs 104. In certain embodiments, switch 118 is a wireless-enabled switch. For example, wireless-enabled switch 118 may be a BTLE-enabled (e.g., Bluetooth® enabled) switch that allows LEDs 104 to be turned on/off wirelessly using a BTLE-enabled device such as a phone or computer. In some embodiments, wireless-enabled switch 118 provides monitoring capabilities for LEDs 104 and panel 102 using the BTLE-enabled device. For example, an app on a BTLE-enabled phone may provide monitoring of power level, LED intensity, and/or other properties of LEDs 104 through switch 118.

In certain embodiments, as shown in FIG. 1, panel 102 include hooks 120. Hooks 120 may be placed along and/or around edges of panel 102. Hooks 120 may be flexible hooks or any hook suitable for hanging or otherwise attaching panel 102 to a wall or other structure. Hooks 120 may be made of material that is non-toxic, inert, and safe for use in a variety of medical spaces. In some embodiments, hooks 120 are removable to allow panel 102 to be coupled to another panel.

In some embodiments, panels 102 have a back surface (e.g., the surface behind LEDs 104) that includes a temporary adhesive backing. The back surface may include, for example, any non-glue based adhesive material that may be used to temporarily couple panel 102 to another surface (e.g., a wall). In some embodiments, the back surface may be Velcro® or another similar temporary connection surface.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

Further modifications and alternative embodiments of various aspects of the embodiments described in this disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as the presently preferred embodiments. Elements and materials may be substituted for those illustrated and described herein, parts and processes may be reversed, and certain features of the embodiments may be utilized independently, all as would be apparent to one skilled in the art after having the benefit of this description. Changes may be made in the elements described herein without departing from the spirit and scope of the following claims.

What is claimed is:

1. A germicidal device, comprising: a panel comprising a plurality of corners;
   a plurality of LEDs embedded in the panel;
   a plurality of lenses embedded in the panel, wherein at least one lens is aligned with at least one LED;
   at least one input connector located on the panel, wherein the at least one input connector is configured to receive an input voltage from a power source;
   a first wiring located on the panel, the first wiring being coupled to the at least one input connector and to one or more of the LEDs;
   a second wiring located on the panel, the second wiring being coupled to the at least one input connector, wherein the second wiring is positioned along edges of the panel in accordance with a perimeter of the panel, and wherein the second wiring is coupled to the at least one input connector at a corner of the panel where the at least one input connector is positioned and to at least one output connector at each of the remaining corners of the panel where the at least one output connector is positioned;
   wherein the at least one input connector is configured to transform the input voltage to a drive voltage and provide the drive voltage to the first wiring and the one or more LEDs, and wherein the at least one input connector is configured to provide the input voltage to the second wiring: and
   the at least one output connector located on the panel, wherein the at least one output connector receives the input voltage from the at least one input connector through the second wiring, and wherein the at least one output connector provides an output voltage that is substantially identical to the input voltage received from the at least one input connector.

2. The device of claim 1, wherein the panel is made of flexible material.

3. The device of claim 1, wherein the LEDs are positioned in an array in the panel.

4. The device of claim 3, wherein the lenses are positioned in an array that corresponds to the array of LEDs.

5. The device of claim 1, wherein the panel comprises two panel portions, the plurality of LEDs being embedded in a first panel portion and the plurality of lenses being embedded in the second panel portion.

6. The device of claim 1, wherein the panel further comprises a plurality of hooks for attaching the panel to a wall or other structure.

7. The device of claim 1, wherein the drive voltage is a different voltage than the input voltage.

8. The device of claim 1, wherein the panel comprises an adhesive backing.

9. The device of claim 1, wherein the LEDs comprise LEDs with a wavelength between about 405 nm and about 450 nm.

10. The device of claim 1, wherein the lenses in the plurality of lenses comprise individually selectable optical properties.

11. The device of claim 1, further comprising a switch coupled to the first wiring and for providing control for the LEDs.

12. The device of claim 1, wherein the panel comprises a rectangular panel.

13. A germicidal device system, comprising: two or more panels, each panel comprising:
   a plurality of corners,
   a plurality of LEDs embedded in the panel, wherein the LEDs are positioned in the panel;
   a plurality of lenses embedded in the panel, wherein at least one lens is aligned with at least one LED;
   at least one input connector located on the panel, wherein the at least one input connector is configured to receive a first voltage;
   a first wiring located on the panel, the first wiring being coupled to the at least one input connector and to one or more of the LEDs;
   a second wiring located on the panel, the second wiring being coupled to the at least one input connector, wherein the second wiring is positioned along edges of the panel in accordance with a perimeter of the panel, and wherein the second wiring is coupled to the at least one input connector at a corner of the panel where the at least one input connector is positioned and to at least one output connector at each of the remaining corners of the panel where the at least one output connector is positioned;
   wherein the at least one input connector is configured to transform the input voltage to a drive voltage and provide the drive voltage to the first wiring and the one or more LEDs, and wherein the at least one input connector is configured to provide the input voltage to the second wiring; and
   the at least one output connector located on the panel, wherein the at least one output connector receives the first voltage from the at least one input connector through the second wiring, and wherein the at least one output connector outputs the first voltage;
   wherein a first panel is configured to be coupled to a second panel by coupling the at least one output connector on the first panel to the at least one input connector on the second panel, and wherein the first panel receives the first voltage from a power source through the at least one input connector on the first panel and provides the first voltage to the second panel, the second panel receiving the first voltage through the at least one input connector on the second panel.

14. The device of claim 13, wherein the panels are made of flexible material.

15. The device of claim 13, wherein the LEDs are positioned in an array in each panel.

16. The device of claim 13, wherein the LEDs comprise LEDs with a wavelength between about 405 nm and about 450 nm.

17. The device of claim 13, wherein the LEDs comprise a combination of LEDs with a wavelength between about 405 nm and about 450 nm and LEDs with a wavelength in the RGB light spectrum.

18. The device of claim 13, wherein the first voltage is a different voltage than the drive voltage.

19. The device of claim 13, wherein the first panel comprises a rectangular panel.

20. The device of claim 13, wherein the second panel provides the drive voltage to the one or more LEDs on the second panel.

* * * * *